(12) United States Patent
Rhee

(10) Patent No.: US 6,962,979 B1
(45) Date of Patent: *Nov. 8, 2005

(54) CROSSLINKABLE BIOMATERIAL COMPOSITIONS CONTAINING HYDROPHOBIC AND HYDROPHILIC CROSSLINKING AGENTS

(75) Inventor: Woonza M. Rhee, Palo Alto, CA (US)

(73) Assignee: Cohesion Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,230

(22) Filed: Jun. 25, 1999

Related U.S. Application Data

(63) Continuation of application No. 08/987,467, filed on Dec. 9, 1997, now abandoned, which is a continuation of application No. 08/403,358, filed on Mar. 14, 1995, now abandoned.

(51) Int. Cl.$^7$ .............................................. C07K 14/78
(52) U.S. Cl. ............................ 530/356; 514/2; 514/801
(58) Field of Search .............................. 530/356; 514/2, 514/801

(56) References Cited

U.S. PATENT DOCUMENTS

| | | | |
|---|---|---|---|
| 4,164,559 A | 8/1979 | Miyata et al. ................. 424/14 |
| 4,695,281 A | 9/1987 | Miyata et al. ................. 623/11 |
| 4,703,108 A | 10/1987 | Silver et al. ................. 530/356 |
| 4,851,513 A | 7/1989 | Devore et al. .............. 530/356 |
| 5,162,430 A | 11/1992 | Rhee et al. ................. 525/54.1 |
| 5,324,775 A | 6/1994 | Rhee et al. ................. 525/54.2 |
| 5,328,955 A | 7/1994 | Rhee et al. ................. 525/54.1 |
| 5,510,418 A | 4/1996 | Rhee et al. ................. 525/54.2 |
| 5,565,519 A | 10/1996 | Rhee et al. ................. 525/54.1 |
| 5,752,974 A * | 5/1998 | Rhee et al. ................. 606/214 |

FOREIGN PATENT DOCUMENTS

| | | |
|---|---|---|
| EP | 0 330 344 A2 | 8/1989 |
| EP | 0 656 214 A1 | 6/1995 |
| EP | 0 668 081 A2 | 8/1995 |
| EP | 0 674 908 A1 | 10/1995 |
| WO | WO 90/05755 | 5/1990 |
| WO | WO 92/13025 | 8/1992 |
| WO | WO 94/01483 | 1/1994 |

OTHER PUBLICATIONS

Shearwater Polymers Catalog, 1997–98 Huntsville, AL.

* cited by examiner

*Primary Examiner*—Christopher S. F. Low
*Assistant Examiner*—Anish Gupla
(74) *Attorney, Agent, or Firm*—Reed IP Law Group

(57) ABSTRACT

The present invention discloses novel crosslinked biomaterial compsotions which are prepared using hydrophobic polymers as a crosslinking agent. Preferred hydrophobic polymers are those that contain two or more reactive succinimidyl groups, including disuccinimidyl suberate, bix (sulfosuccinimidyl) suberate, and dithiobis (succinimidylpropionate). Crosslinked biomaterial compositions prepared using mixtures of hydrophobic and hydrophilic crosslinking agents are also disclosed. The compositions of the present invention can be used to prepare formed implants for use in a variety of medical applications.

54 Claims, 10 Drawing Sheets

US 6,962,979 B1

CROSSLINKABLE BIOMATERIAL COMPOSITIONS CONTAINING HYDROPHOBIC AND HYDROPHILIC CROSSLINKING AGENTS

CROSS-REFERENCE TO RELATED APPLICATIONS

This application is a continuation of U.S. application Ser. No. 08/987,467, filed Dec. 9, 1997, abandoned, which was a continuation of U.S. application Ser. No. 08/403,358, filed Mar. 14, 1995, also abandoned, the disclosures of which are incorporated-herein-by-reference.

FIELD OF THE INVENTION

This invention relates generally to the use of hydrophobic crosslinking agents to prepare injectable or implantable crosslinked biomaterial compositions for use in a variety of therapeutic applications. Specifically, this invention relates to crosslinked biomaterial compositions prepared using hydrophobic crosslinking agents containing two or more succinimidyl groups, such as disuccinimidyl suberate, bis(sulfosuccinimidyl) suberate, or dithiobis(succinimidylpropionate). Also provided are unique crosslinked biomaterial compositions prepared using mixtures of hydrophobic and hydrophilic crosslinking agents. The compositions of the invention are particularly useful in the preparation of formed implants for a variety of medical uses.

BACKGROUND OF THE INVENTION

U.S. Pat. No. 5,162,430, issued Nov. 10, 1992 to Rhee et al., and commonly owned by the assignee of the present application, discloses collagen-synthetic polymer conjugates and methods of covalently binding collagen to synthetic hydrophilic polymers. Commonly owned U.S. Pat. No. 5,328,955, issued Jul. 12, 1994 to Rhee et al., discloses various activated forms of polyethylene glycol and various linkages which can be used to produce collagen-synthetic polymer conjugates having a range of physical and chemical properties. Commonly owned U.S. Pat. No. 5,324,775, issued June 28, 1994 to Rhee et al., discloses biocompatible polymer conjugates prepared by covalently binding biologically inert, biocompatible polymers to synthetic hydrophilic polymers.

Commonly owned, copending U.S. application Ser. No. 08/146,843, filed Nov. 3, 1993, discloses conjugates comprising various species of glycosaminoglycan covalently bound to synthetic hydrophilic polymers, which are optionally bound to collagen as well. Commonly owned, copending U.S. application Ser. No. 08/147,227, filed Nov. 3, 1993, discloses collagen-polymer conjugates comprising chemically modified collagens such as, for example, succinylated collagen or methylated collagen, covalently bound to synthetic hydrophilic polymers to produce optically clear materials for use in ophthalmic or other medical applications.

Hydrophobic crosslinking agents such as such as disuccinimidyl suberate, bis(sulfosuccinimidyl) suberate, and dithiobis(succinimidylpropionate) have a long history of use for crosslinking biologically active peptides, as described in the 1992 Pierce (Rockford, Ill.) catalog.

All publications cited above and herein are incorporated herein by reference to describe and disclose the subject matter for which it is cited.

We now disclose a detailed description of preferred embodiments of the present invention, including crosslinked biomaterial compositions prepared using various hydrophobic crosslinking agents and crosslinked biomaterial compositions prepared using mixtures of hydrophobic and hydrophilic crosslinking agents.

SUMMARY OF THE INVENTION

Figure 1:
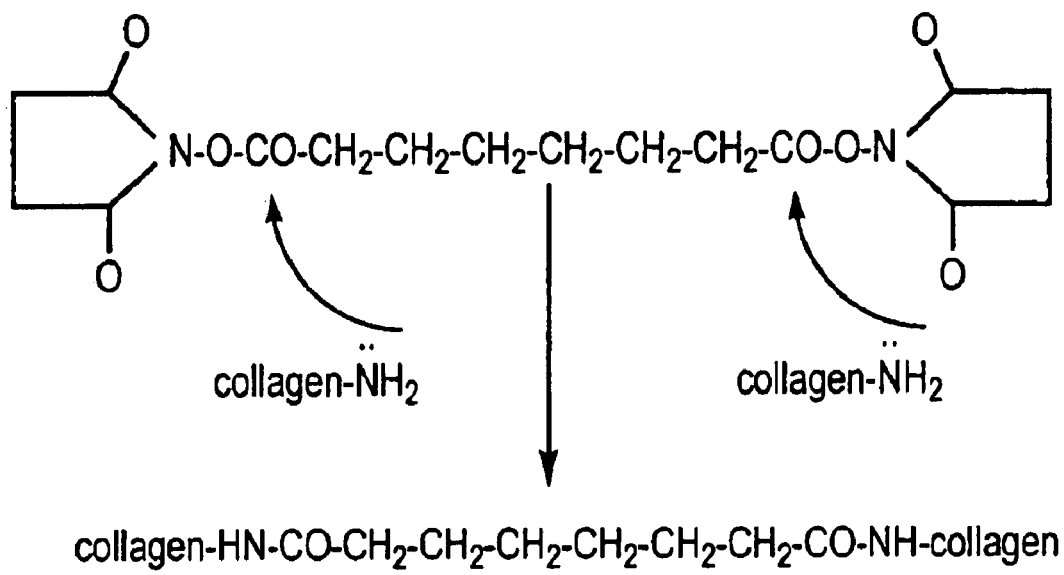
FIG. 1 shows the structural formula for disuccinimidyl suberate (DSS), and a reaction product obtained by reacting DSS with collagen.
Figure 2:
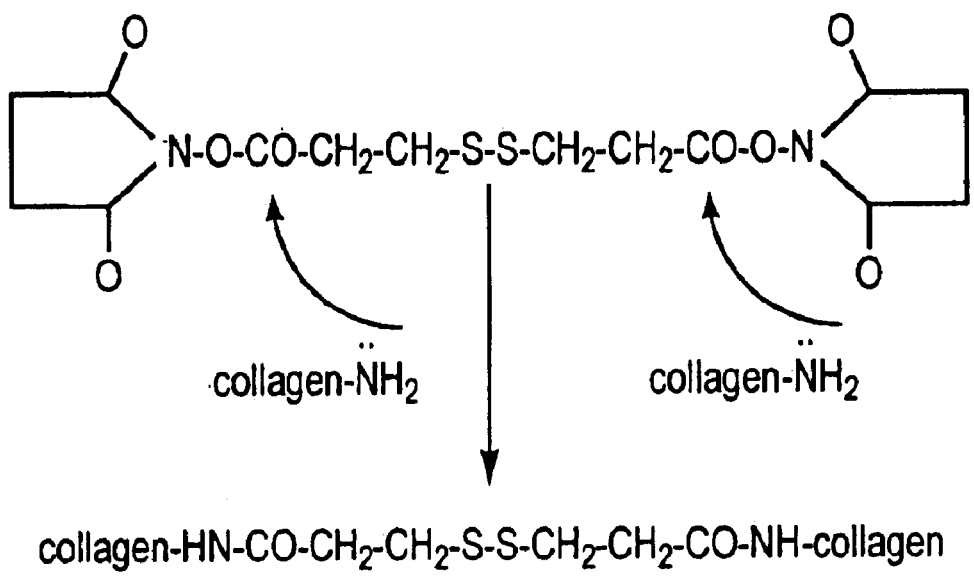
FIG. 2 shows the structural formula for dithiobis(succinimidyl propionate) (DSP), and a reaction product obtained by reacting DSP with collagen.
Figure 3:
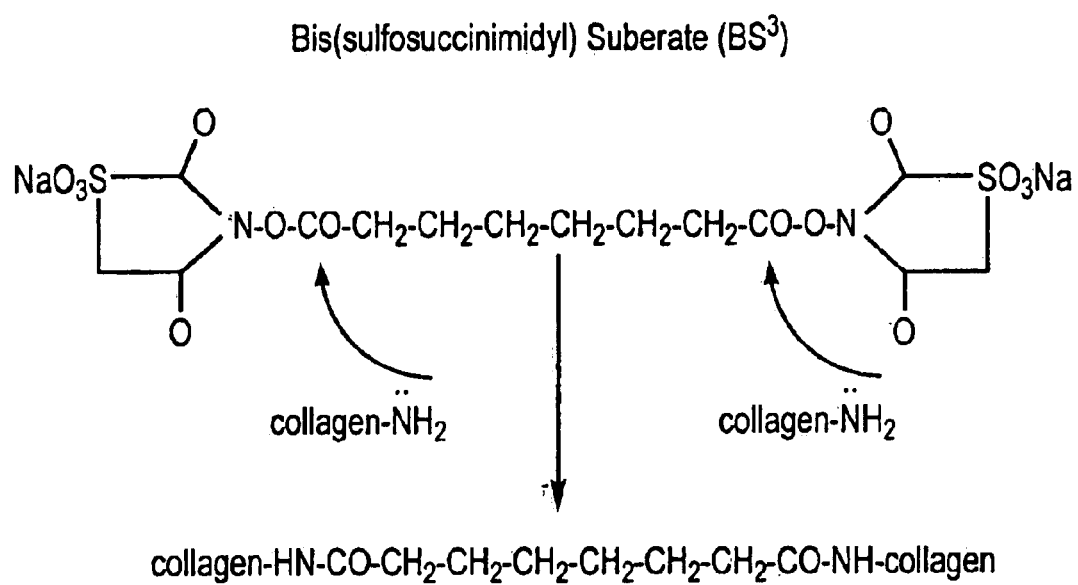
FIG. 3 shows the structural formula for bis(sulfosuccinimidyl)suberate ($BS^3$), and a reaction product obtained by reacting $BS^3$ with collagen.
Figure 4:
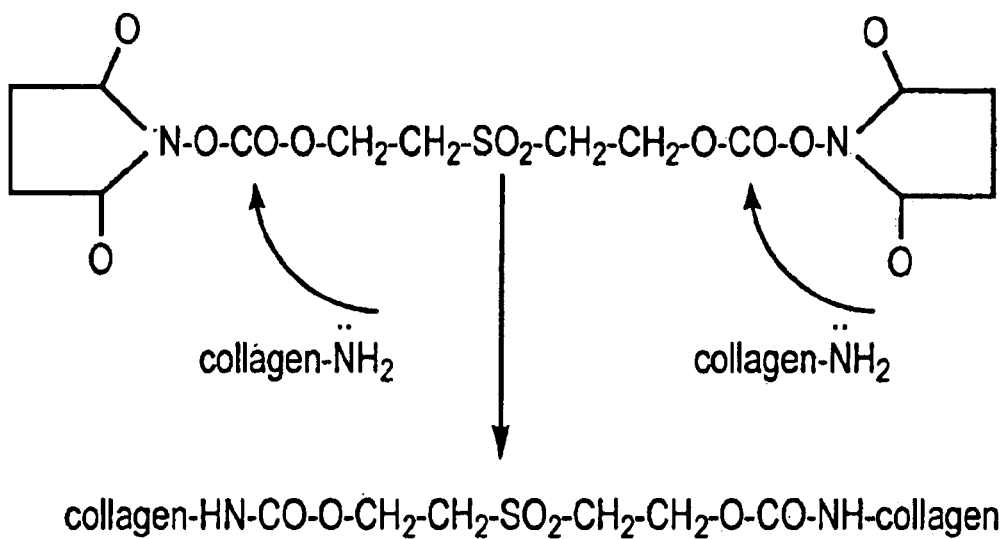
FIG. 4 shows the structural formula for bis(2-succinimidooxycarbonyl-oxy)ethyl sulfone (BSOCOES), and a reaction product obtained by reacting BSOCOES with collagen.
Figure 5:
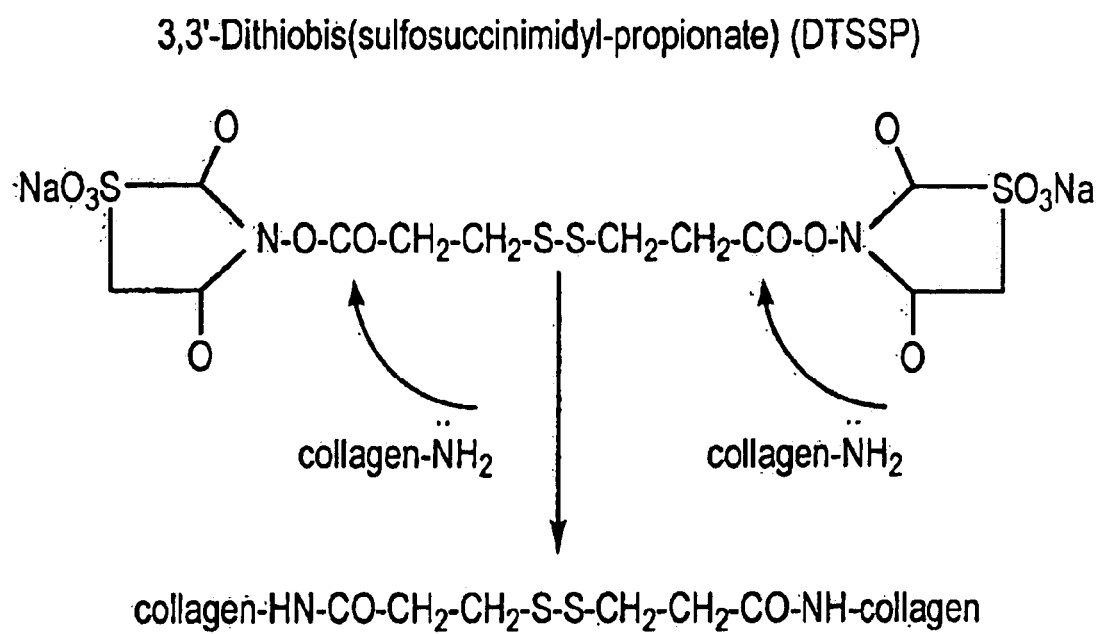
FIG. 5 shows the structural formulas for 3,3'-dithiobis(sulfosuccinimidyl propionate) (DTSSP), and a reaction product obtained by reacting DTSSP with collagen.

In our earlier patents and applications, we disclosed various crosslinked biomaterial compositions prepared using synthetic hydrophilic polymers, preferably functionally activated polyethylene glycols (PEGs), as the crosslinking agent. In accordance with the present invention, we have since discovered that various hydrophobic polymers containing two or more succinimidyl groups, such as disuccinimidyl suberate, bis(sulfosuccinimidyl) suberate, or dithiobis(succinimidyl-propionate), can be used to crosslink various biomaterials such as collagen and glycosaminoglycans. We have also discovered that certain hydrophobic polymers, such as polyacids, can be derivatized to contain two or more succinimidyl groups and, in the derivatized form, can be used to crosslink collagen and glycosaminoglycans. Furthermore, we have discovered that unique crosslinked biomaterial compositions can be prepared by using a mixture of hydrophobic and hydrophilic crosslinking agents.

The present invention pertains to conjugates comprising biomaterials covalently bonded to hydrophobic polymers, wherein the hydrophobic polymer contains two or more succinimidyl groups prior to bonding with the biomaterial. Included in the invention are conjugates comprising biomaterials covalently bonded to hydrophobic polymers, in which the hydrophobic polymer has been chemically derivatized to contain two or more succinimidyl groups prior to bonding with the biomaterial. Heterogeneous crosslinked biomaterial compositions are also disclosed which comprise a biomaterial (or mixtures of different species of biomaterials), a hydrophobic crosslinking agent, and a hydrophilic crosslinking agent. Further, in accordance with the invention, formed implants are prepared using the conjugates and compositions of the invention.

The compositions of the present invention have many unique and unexpected features when compared with the previously disclosed crosslinked biomaterial compositions prepared using only hydrophilic crosslinking agents. An important feature of the compositions of the present invention (when compared to previous crosslinked biomaterial compositions) is slower degradation, resulting in greater chemical stability, which may lead to increased in vivo persistence. Additional features and advantages of the invention will become apparent upon reading the detailed description of the invention which follows.

Definitions

It must be noted that, as used in this specification and the appended claim, the singular forms "a", "an", and "the" include plural referents unless the context clearly dictates otherwise. For example, reference to "a conjugate" includes one or more conjugate molecules, reference to "an article" includes one or more different types of articles known to those skilled in the art and reference to "the collagen" includes mixtures of different types of collagens and so forth.

Specific terminology of particular importance to the description of the present invention is defined below:

The term "atelopeptide collagen" refers to collagens which have been chemically treated or otherwise processed to remove the telopeptide regions, which are known to be responsible for causing an immune response in humans to collagens from other animal, such as bovine, sources.

The term "biomaterial" as used herein refers in general to biocompatible, naturally occurring polymers, including collagen, gelatin, and polysaccharides such as glycosaminoglycans.

The terms "chemically conjugated" and "conjugated" as used herein mean attached through a covalent chemical bond. In the practice of the invention, a hydrophobic polymer and a biomaterial may be covalently conjugated to each other by means of a reactive succinimidyl group on the hydrophobic polymer.

The term "chemical crosslinking agent" as used herein refers to any chemical agent capable of covalently binding biomaterials, such as collagen, glycosaminoglycans, and mixtures thereof, to form a crosslinked biomaterial network.

The term "collagen" as used herein refers to all types and forms of collagen, including those which have been recombinantly produced, extracted from naturally occurring sources (such as bovine corium or human placenta), processed, or otherwise modified.

The term "collagen suspension" refers to a suspension of noncrosslinked or crosslinked collagen fibers in an aqueous carrier, such as water or phosphate-buffered saline (PBS) solution.

The term "collagen-synthetic polymer" refers to collagen covalently bonded to a synthetic hydrophilic polymer. For example, "PEG-collagen" denotes a composition of the invention wherein molecules of collagen are covalently bonded to molecules of polyethylene glycol (PEG).

The term "difunctionally activated" refers to synthetic hydrophilic polymer molecules which have been chemically derivatized so as to have two functional groups capable of reacting with primary amino groups on biocompatible polymer molecules, such as collagen or deacetylated glycosaminoglycans. The two functional groups on a difunctionally activated synthetic hydrophilic polymer are generally located at opposite ends of the polymer chain. Each functionally activated group on a difunctionally activated synthetic hydrophilic polymer molecule is capable of covalently binding with a biocompatible polymer molecule, thereby effecting crosslinking between the biocompatible polymer molecules.

The term "dry" means that substantially all unbound water has been removed from a material.

The term "fibrillar collagen" refers to collagens in which the triple helical molecules aggregate to form thick fibers due to intermolecular charge and hydrophobic interactions.

The term "functionally activated" refers to synthetic hydrophilic polymers which have been chemically derivatized so as to have one or more functional group capable of reacting with primary amino groups on biocompatible polymer molecules.

The term "in situ" as used herein means at the site of administration.

The term "in situ crosslinking" as used herein refers to crosslinking of a biocompatible polymer implant following implantation to a tissue site on a human or animal subject, wherein at least one functional group on the synthetic polymer is covalently conjugated to a biocompatible polymer molecule in the implant, and at least one functional group on the synthetic polymer is free to covalently bind with, other biocompatible polymer molecules within the implant, or with collagen molecules within the patient's own tissue.

The term "molecular weight" as used herein refers to the weight average molecular weight of a number of molecules in any given sample, as commonly used in the art. Thus, a sample of PEG 2000 might contain a statistical mixture of polymer molecules ranging in weight from, for example, 1500 to 2500, with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20,000.

The term "multifunctionally activated" refers to synthetic hydrophilic polymers which have been chemically derivatized so as to have two or more functional groups which are located at various sites along the polymer chain and are capable of reacting with primary amino groups on biocompatible polymer molecules. Each functional group on a multifunctionally activated synthetic hydrophilic polymer molecule is capable of covalently binding with a biocompatible polymer molecule, thereby effecting crosslinking between the biocompatible polymer molecules. Types of multifunctionally activated hydrophilic synthetic polymers include difunctionally activated, tetrafunctionally activated, and star-branched polymers.

The term "noncrosslinked collagen" refers to collagens that have not been previously crosslinked using chemical crosslinking agents. Such noncrosslinked collagens may include both fibrillar and nonfibrillar collagens.

The term "nonfibrillar collagen" refers to collagens in which the triple helical molecules do not aggregate to form thick fibers, such that a composition containing nonfibrillar collagen will be optically clear.

The terms "synthetic hydrophilic polymer" or "synthetic polymer" refer to polymers which have been synthetically produced and which are hydrophilic, but not necessarily water-soluble. Examples of synthetic hydrophilic polymers which can be used in the practice of the present invention are polyethylene glycol (PEG), polyoxyethylene, polymethylene glycol, poly-trimethylene glycols, polyvinylpyrrolidones, polyoxyethylene-polyoxypropylene block polymers and copolymers, and derivatives thereof. Naturally occurring polymers such as proteins, starch, cellulose, heparin, hyaluronic acid, and derivatives thereof are expressly excluded from the scope of this definition.

The term "tissue augmentation" as used herein refers to the replacement or repair of defects in the soft or hard tissues of a human body.

Except as otherwise defined above, all technical and scientific terms used herein have the same meaning as commonly understood by one of ordinary skill in the art to which this invention belongs. Although any methods and materials similar or equivalent to those described herein may be useful in the practice or testing of the present invention, only the preferred methods and materials are described below.

DETAILED DESCRIPTION OF THE PREFERRED EMBODIMENTS OF THE INVENTION

In accordance with the present invention, unique crosslinked biomaterial compositions are prepared using hydrophobic crosslinking agents, or mixtures of hydrophilic and hydrophobic crosslinking agents. In order to prepare the crosslinked biomaterial compositions of the present invention, it is first necessary to provide one or more biomaterials and a hydrophobic crosslinking agent.

Preferred Biomaterials

Any biomaterial that has, or can be chemically derivatized to have, primary amino ($-NH_2$) groups capable of binding with hydrophobic or hydrophilic crosslinking agents according to the methods of the invention may be used to prepare the crosslinked biomaterial compositions of the invention. Preferred biomaterials for use in the practice of the present invention include all types of collagen and glycosaminoglycans, and mixtures thereof.

In general, collagen from any source may be used in the practice of the present invention; for example, collagen may be extracted and purified from human or other mammalian source, or may be recombinantly or otherwise produced. Collagen of any type, including, but not limited to, types I, II, III, IV, or any combination thereof, may be used, although type I is generally preferred. Either atelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen. The collagen should be in a pharmaceutically pure form such that it can be incorporated into a human body without generating any significant immune response.

Collagens for use in the present invention may be in the fibrillar or nonfibrillar form. Fibrillar collagens are generally preferred for tissue augmentation applications due to their increased persistence in vivo. Nonfibrillar collagens, including chemically modified collagens such as succinylated or methylated collagen, may be preferable in certain situations, such as ophthalmic applications where an optically transparent material is required. Succinylated and methylated collagens can be prepared according to the methods described in U.S. Pat. No. 4,164,559 (which is hereby incorporated by reference in its entirety). Noncrosslinked collagens for use in the present invention are normally in aqueous suspension at a concentration between about 20 mg/ml to about 120 mg/ml, preferably, between about 30 mg/ml to about 80 mg/ml. Fibrillar collagen in suspension at various collagen concentrations is commercially available from Collagen Corporation under the trademark Zyderm® I Collagen (35 mg/ml) and Zyderm II Collagen (65 mg/ml).

Collagen in its native state contains lysine residues having primary amino groups capable of covalently binding with the hydrophobic and hydrophilic crosslinking agents of the invention and therefore need not be chemically modified in any way prior to reaction with the desired crosslinking agent according to the methods of the invention.

Although intact collagen is preferred, denatured collagen, commonly known as gelatin, can also be used in the preparation of the compositions of the invention.

Glycosaminoglycans for use in the present invention include, without limitation, hyaluronic acid, chondroitin sulfate A, chondroitin sulfate C, dermatan sulfate, keratan sulfate, keratosulfate, chitin, chitosan, heparin, and derivatives or mixtures thereof. Glycosaminoglycans must generally be modified, such as by deacetylation or desulfation, in order to provide primary amino groups capable of binding with functional groups on hydrophobic and hydrophilic crosslinking agent according to the methods of the present invention. Methods for chemically modifying glycosaminoglycans by deacetylation and/or desulfation are described in commonly owned, copending U.S. application Ser. No. 08/146,843, filed Nov. 3, 1993. In general, glycosaminoglycans can be deacetylated, desulfated, or both, as applicable, by the addition of a strong base, such as sodium hydroxide, to the glycosaminoglycan. Deacetylation and/or desulfation provides primary amino groups on the glycosaminoglycan which are capable of covalently binding with hydrophobic or hydrophilic crosslinking agents according to the methods of the present invention.

Mixtures of various species of glycosaminoglycan, various types of collagen, or mixtures of various glycosaminoglycans with collagen may be used to prepare the crosslinked biomaterial compositions of the present invention.

If the final composition is intended for incorporation into the body of a human or animal subject, biomaterials for use in the present invention must be in pharmaceutically pure form, or capable of being purified to be in pharmaceutically pure form.

Preparation of Hydrophobic Crosslinking Agents

In order to prepare the crosslinked biomaterial compositions of the present invention, it is first necessary to provide a hydrophobic polymer which contains, or can be derivatized to contain, two or more succinimidyl groups. As used herein, the term "hydrophobic polymer" refers to polymers which contain a relatively small proportion of oxygen or nitrogen atoms. As used herein, the term "containing two or more succinimidyl groups" is meant to encompass hydrophobic polymers which are commercially available containing two or more succinimidyl groups, as well as those that must be chemically derivatized to contain two or more succinimidyl groups. As used herein, the term "succinimidyl group" is intended to encompass sulfosuccinimidyl groups and other such variations on the "generic" succinimidyl group. The presence of the sodium sulfate moiety on the sulfosuccinimidyl group serves to increase the solubility of the polymer.

Hydrophobic polymers for use in the present invention preferably contain, or can be derivatized to contain, two or more succinimidyl groups, most preferably, two, three, or four succinimidyl groups. These succinimidyl groups are highly reactive with biomaterials containing primary amino (—$NH_2$) groups, such as collagen and various glycosaminoglycans and glycosaminoglycan derivatives.

Hydrophobic polymers which already contain two or more reactive succinimidyl groups include, without limitation, disuccinimidyl suberate (DSS), bis (sulfosuccinimidyl) suberate ($BS^3$), dithiobis (succinimidylpropionate) (DSP), bis(2-succinimidooxycarbonyloxy)ethyl sulfone (BSOCOES), and 3,3'-dithiobis(sulfosuccinimidylpropionate) (DTSPP), and their analogs and derivatives. The above-referenced polymers are commercially available from Pierce (Rockford, Ill.)+under catalog Nos. 21555, 21579, 22585, 21554, and 21577, respectively. Structural formulas for the above-referenced polymers, as well as generalized reaction products obtained by reacting each of these polymers with collagen, are shown in FIGS. 1–5, respectively.

Certain polymers, such as polyacids, can be derivatized to contain two or more reactive succinimidyl groups. Polyacids for use in the present invention include, without limitation, trimethylolpropane-based tricarboxylic acid, di(trmethylol propane)-based tetracarboxylic acid, heptanedioic acid, octanedioic acid (suberic acid), and hexadecanedioic acid (thapsic acid). Many of these polyacids are commercially available from DuPont Chemical Company.

According to a general method, polyacids can be chemically derivatized to contain two or more succinimidyl groups by reaction with an appropriate molar amount of N-hydroxysuccinimide (NHS) in the presence of N,N'-dicyclohexylcarbodiimide (DCC).

Figure 6:
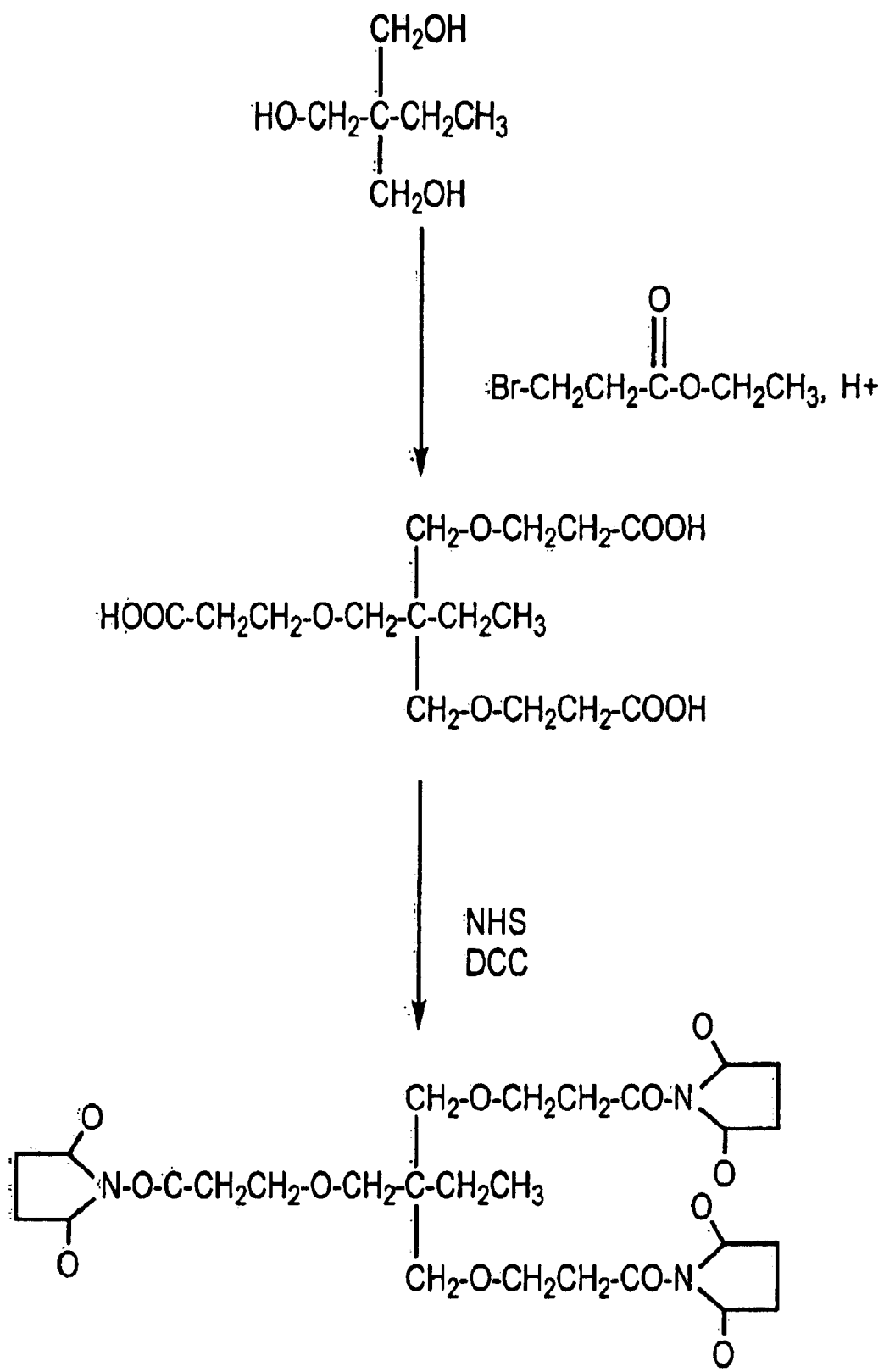
FIG. 6 shows a reaction scheme for derivatizing trimethylpropane to its tricarboxylic acid form, then further derivatizing this tricarboxylic acid from by reacting it with N-hydroxysuccinimide (NHS) in the presence of N,N'dicyclohexylcarbodiimide (D CC) to produce a trifunctional crosslinking agent.
Figure 7:
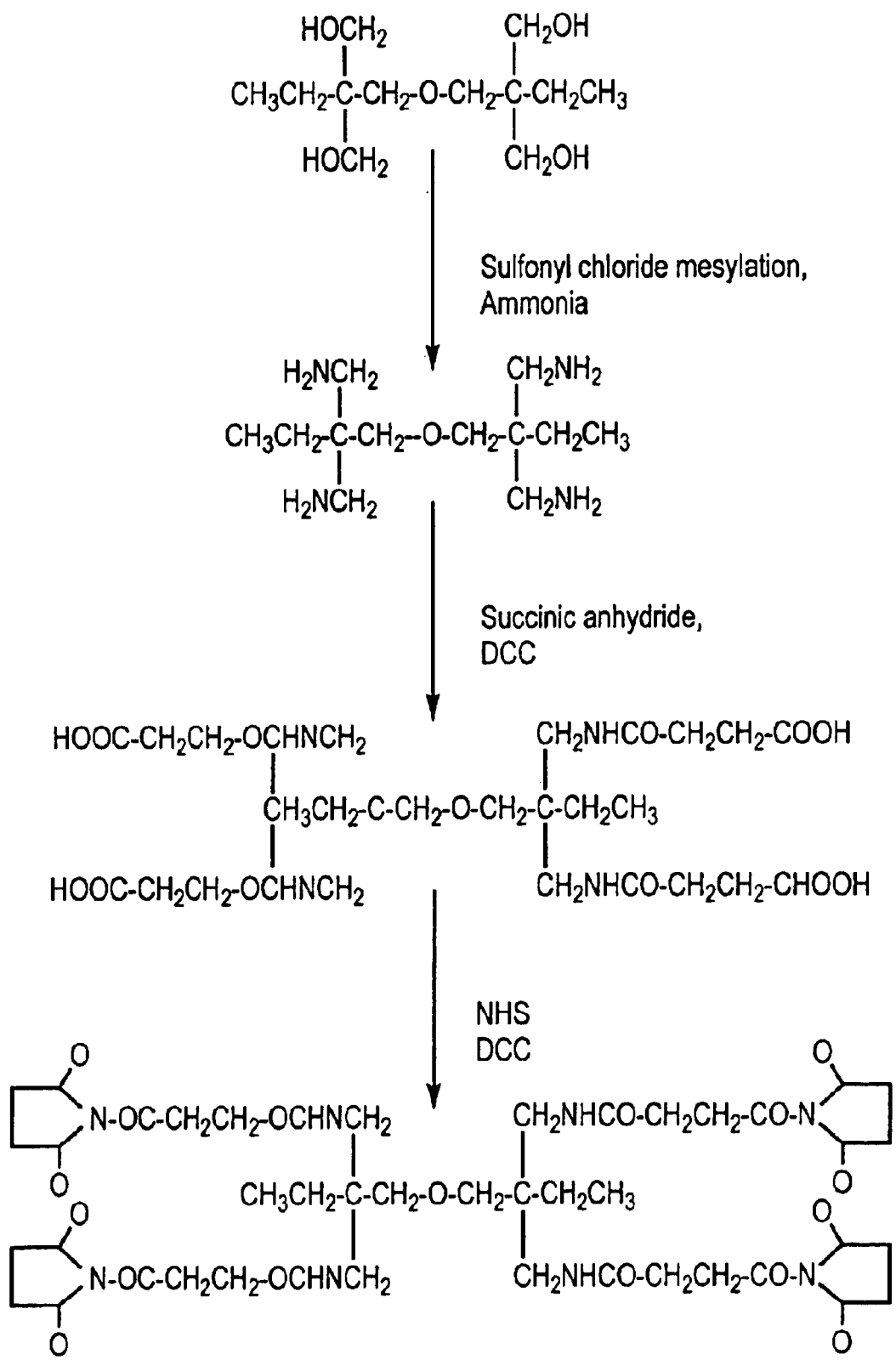
FIG. 7 shows a reaction scheme for derivatizing di(trimethylpropane) to its tetracarboxylic acid form, then further derivatizing this tetracarboxylic acid form by reacting it with NHS in the presence of DCC to produce a tetrafunctional crosslinking agent.

Polyalcohols such as trimethylolpropane and di(trimethylol propane) can be converted to carboxylic acid form using various methods, then further derivatized by the addition of succinimidyl groups, as shown in FIGS. 6 and 7.

Trimethylolpropane can be derivatized to tricarboxylic acid form, then further derivatized by reaction with NHS in the presence of DCC to produce a trifunctional crosslinking agent (ie., a compound having three succinimidyl groups available for reaction with various biomaterials), as shown in FIG. 6.

Di(trimethylol propane) can be derivatized to tetracarboxylic acid form, then further derivatized by reaction with NHS in the presence of DCC to produce a tetrafunctional crosslinking agent, as shown in FIG. 7.

Other polyacids can be chemically derivatized to contain two or more reactive succinimidyl groups using methods similar to those shown in FIGS. 6 and 7 for trimethylolpropane-based tricarboxylic acid and di(trimethylolpropane)-based tetracarboxylic acid, respectively. Polyacids such as heptanedioic acid (HOOC—$(CH_2)_5$—COOH), octanedioic acid (HOOC—$(CH_2)_6$—COOH), and hexadecanedioic acid (HOOC—$(CH_2)_{14}$—COOH) are derivatized by the addition of succinimidyl groups to produce difunctional crosslinking agents.

Polyamines such as ethylenediamine ($H_2N$—$CH_2$ $CH_2$—$NH_2$), tetramethylenediamine ($H_2N$—$(CH_2)_4$—$NH_2$), pentamethylenediamine (cadaverine) ($H_2N$—$(CH_2)_5$—$NH_2$), hexamethylenediamine ($H_2N$—$(CH_2)_6$—$NH_2$), bis(2-hydroxyethyl)amine (HN-$(CH_2CH_2OH)_2$), bis(2) aminoethyl)amine (HN—$(CH_2CH_2NH_2)_2$), and tris(2-aminoethyl)amine (N—$(CH_2CH_2NH_2)_3$) can be chemically derivatized to polyacids, which can then be derivatized to contain two or more succinimidyl groups by reacting with the appropriate molar amounts of N-hydroxysuccinimide in the presence of DCC according to the general method described above for polyacids. Many of these polyamines are commercially available from DuPont Chemical Company.

Preferred hydrophobic polymers for use in the invention, whether they are commercially available containing two or more succinimidyl groups or must be chemically derivatized to contain two or more succinimidyl groups, generally have a carbon chain that is no longer than about 14 carbons. Polymers having carbon chains substantially longer than 14 carbons generally have very poor solubility in aqueous solutions and, as such, have very long reaction times when mixed with an aqueous solution of a biomaterial such as collagen.

Preparation of Crosslinked Biomaterial Compositions Using Hydrophobic Crosslinking Agents In a general method for preparing the crosslinked biomaterial compositions of the invention, a biomaterial which contains, or has been chemically derivatized to contain, primary amino groups is mixed with a hydrophobic polymer which contains, or has been derivatized to contain, two or more succinimidyl groups capable of crosslinking the biomaterial by reacting with nucleophilic primary amino groups on the biomaterial. The hydrophobic crosslinking agent can be stored and used in either dry form or in solution, but is preferably used in dry form. The crosslinking agent may be mixed with either an aqueous solvent or a hydrophobic solvent prior to mixing with the biomaterial. If an aqueous solvent is used, the crosslinking agent should be mixed with the solvent just prior to use, as the succinimidyl groups are reactive with neutrophiles such as oxygen and water. Exposure to aqueous solvents for extended periods of time will result in loss of crosslinking ability due to hydrolysis of the crosslinking agent.

The biomaterial and hydrophobic crosslinking agent (in dry form) may be stored in separate syringes and then mixed using syringe-to-syringe mixing techniques, as follows: the biomaterial and crosslinking agent are mixed by connecting the syringe containing the biomaterial with the syringe containing the crosslinking agent using a syringe connector (such as a three-way stopcock) and passing the material back and forth between the two syringes until the material is adequately mixed (usually requiring a minimum of about 20 passes, with one pass being counted each time the volume of material passes through the syringe connector). During the mixing process, crosslinking is initiated between molecules of the biomaterial and the crosslinking agent.

The concentration of the hydrophobic crosslinking agent used in the practice of the invention will vary depending upon a number of factors, including the type and molecular weight of the crosslinking agent used, the type and concentration of biomaterial used, and the degree of crosslinking desired. In general, we have found that hydrophobic crosslinking agent concentrations in the range of about 0.1 to about 2 percent by weight of the final composition are preferred to prepare the crosslinked biomaterial compositions of the present invention.

Preparation of Heterogeneous Crosslinked Biomaterial Compositions Using Mixtures of Hydrophobic and Hydrophilic Crosslinking Agents In a general method for preparing the heterogeneous crosslinked biomaterial compositions of the invention, a biomaterial which contains, or has been chemically derivatized to contain, primary amino groups is combined and allowed to covalently bond with a mixture of hydrophobic and hydrophilic crosslinking agents. Preferably, the mixture of hydrophobic and hydrophilic crosslinking agents is stored and used in dry form, to prevent loss of crosslinking activity due to hydrolysis. The hydrophobic and hydrophilic crosslinking agents will generally not react with one other because both crosslinking agents contain the same reactive groups (i e., succinimidyl groups) which preferentially bind to primary amino groups on various biomaterials such as collagen and derivatized glycosaminoglycans.

In an alternative method, the biomaterial is mixed first with either the hydrophobic or hydrophilic crosslinking agent, then (preferably in rapid succession, before gellation occurs), with the other type of crosslinking agent.

As used herein, the term "hydrophobic polymer" refers to polymers which contain a relatively small proportion of oxygen or nitrogen atoms. Hydrophobic polymers which contain, or have been derivatized to contain, two or more reactive succinimidyl groups are the preferred hydrophobic crosslinking agents for use in the preparation of the heterogeneous crosslinked biomaterial compositions of the invention.

As used herein, the term "hydrophilic polymer" refers to polymers which contain a relatively large proportion of oxygen and/or nitrogen atoms, which serve to attract water molecules for hydrogen bonding. Synthetic hydrophilic polymers, such as functionally activated polyethylene glycols, are the preferred hydrophilic crosslinking agents for use in the preparation of the heterogeneous crosslinked biomaterial compositions of the present invention. Various activated forms of polyethylene glycol are described in detail in commonly owned U.S. Pat. No. 5,328,955 (the disclosure of which is incorporated herein by reference) and copending U.S. application Ser. No. 08/344,040, filed Nov. 23, 1994.

Synthetic hydrophilic polymers for use in the present invention are preferably multifunctionally activated and, more preferably, difunctionally activated. Preferred synthetic hydrophilic polymers are difunctionally activated forms of PEG succinimidyl glutarate (SG-PEG), PEG succinimidyl (SE-PEG; referred to only as "S-PEG" in the '955 patent), PEG succinimidyl succinamide (SSA-PEG), and PEG succinimidyl carbonate (SC-PEG). Reaction of SG-PEG with a biomaterial such as collagen results in covalently bound conjugates containing an ester linkage; reaction of SE-PEG (n=1–3) or SC-PEG (n=0) with a biomaterial results in conjugates containing an ether linkage; and reaction of SSA-PEG (n=1–10) with a biomaterial results in conjugates containing an amide linkage. The amide and ether linkages are generally less susceptible to hydrolysis than the ester linkage, and therefore may result in crosslinked biomaterial compositions having greater stability and persistence in vivo, depending on the environment into which the implant material is placed. Ether linkages are susceptible to oxidation, and may be sensitive to degradation by free radicals.

Many of the activated forms of poly ethylene glycol described above are now available commercially from Shearwater Polymers, Huntsville, Ala., and from Union Carbide, South Charleston, West Va.

Use and Administration

The crosslinked biomaterial compositions of the present invention are particularly useful in the preparation of formed implants for use in a variety of medical applications, including various artificial organs and tubular implants for use as vascular grafts and/or stents. In a general method for preparing a formed implant, a biomaterial/crosslinking agent reaction mixture, prepared as described above, is extruded into molds of various sizes and shapes, preferably before significant crosslinking has occurred between the biomaterial and the crosslinking agent (or mixture of crosslinking agents). This period of time will vary depending upon the type and concentration of both the biomaterial and the crosslinking agent(s) used, but is generally within the range of about 5 to about 60 minutes. The material should be removed from the mold only after adequate time has elapsed to allow for equilibrium crosslinking to occur between the biomaterial and crosslinking agent(s). If necessary, residual, unbound crosslinking agent can be removed from the implant prior to its incorporation into the body of a patient.

The biomaterial/crosslinking agent mixture can also be applied to (for example, by extrusion, dipping, brushing, or painting) onto one or more surface of a preformed synthetic implant, such as a bone prosthesis or synthetic vascular graft or stent, and allowed to crosslink in place, thereby providing a crosslinked, nonimmunogenic biomaterial coating on the surface of the implant. Alternatively, all or part of a preformed synthetic implant can be dipped into a container holding the biomaterial/crosslinking agent reaction solution.

The biomaterial/crosslinking agent mixture can be extruded in the shape of a string and allowed to crosslink in that configuration. When the strings are fully crosslinked, they can be dried to remove substantially all unbound water. The dried strings can be inserted through a needle to a dermal site in need of correction (such as a depressed scar or wrinkle) in order to provide soft tissue augmentation. The dried strings can also be chopped into fine pieces, suspended in a nonaqueous carrier, and injected to a tissue site in need of augmentation, which may be a dermal site or other soft tissue site such as an inadequately functioning sphincter (e.g., urinary, anal, or esophageal sphincter). When exposed to biological fluids, the crosslinked strings will rehydrate in situ and swell to approximately five times their dried diameter. The dried strings can also be used as suture materials, or braided, knit, or woven to provide biomaterials for tendon or ligament repair or replacement.

A suitable particulate material, such as ceramic particles, can be mixed with the biomaterial prior to mixing with the crosslinking agent to provide a material suitable for hard tissue augmentation, such as the repair or replacement of bone or cartilage. These materials can be administered in fluid form (prior to crosslinking) to the site of a bone or cartilage defect and allowed to crosslink in place, or can be used to prepare formed bone or cartilage implants (using techniques similar to those described above for the preparation of formed implants for soft tissue repair) which can then be molded or cut to the desired size and shape.

The crosslinked biomaterial compositions of the invention can also be used as injectable formulations in the augmentation of soft or hard tissues of the body. Following mixing of the biomaterial and the crosslinking agent(s), the reaction mixture should be injected to a tissue site before significant crosslinking has occurred, to prevent blockage of the syringe needle with the crosslinked composition. If the material is injected to a tissue site before equilibrium crosslinking has occurred, functional groups on the crosslinking agent(s) may bind to collagen molecules in the host tissue, thereby providing biological anchoring of the biomaterial to the host tissue. Implants which have been "biologically anchored" to host tissue are more difficult to displace and therefore may show greater persistence in vivo than currently available injectable biomaterial compositions.

Biologically active agents, such as cytokines or growth factors, can be incorporated into the compositions of the invention, either by simple admixture, or by covalently binding the active agent to the crosslinking agent prior to combining the crosslinking agent with the biomaterial. The active agents may serve to recruit cells to the area of the implant, further anchoring the implant to host tissue, and may accelerate wound healing when administered to a wound site.

EXAMPLES

The following examples are put forth so as to provide those of ordinary skill in the art with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1

Preparation and Characterization of Crosslinked Collagen Compositions Using Hydrophobic Crosslinking Agents Fibrillar collagen (Zyderm® I Collagen, available from Collagen Corporation, Palo Alto, Calif.) and methylated (nonfibrillar) collagen (prepared by reacting fibrillar collagen with methanol for approximately 1–3 days at 21° C.) were crosslinked using disuccinimidyl suberate (DSS), bis (sulfosuccinimidyl) suberate ($BS^3$), difunctionally activated SE-PEG (n=2, 3800 MW), and difunctionally activated SG-PEG (3800 MW).

The fibrillar collagen formulations were prepared by mixing the contents of a 1-cc syringe containing 1.0 cc of Zyderm Collagen (35 mg/ml collagen concentration) with the contents of a 1-cc syringe containing one of the following crosslinking agents in the quantity specified:

3 mg of DSS;

3 mg of $BS^3$;

5 mg of SE-PEG; or 5 mg of SG-PEG.

The methylated collagen formulations were prepared by mixing the contents of a 1-cc syringe containing 1.0 cc of methylated collagen (21 mg/ml collagen concentration) with the contents of a 1-cc syringe containing one of the following crosslinking agents in the quantity specified:

3 mg of DSS;

3 mg of $BS^3$;

10 mg of SE-PEG; or 10 mg of SG-PEG.

All of the crosslinking agents were used in dry form. The collagen and crosslinking agent were mixed by passing the, material between the two syringes using a 3-way stopcock, employing about 40 to 50 passes of material between the syringes. Once adequate mixing of the collagen and crosslinking agent had been achieved, the material was transferred into one syringe and incubated at 37° C. for approximately. 16 hours.

Each of the crosslinked collagen materials prepared as described above was extruded out of the plunger end of its syringe. The resulting crosslinked cylindrical gels were then sectioned into 5-mm thick disks. Each of the formulations was then evaluated according to some or all of the following test methods: differential scanning calorimetry (DSC), solubilization in 1 mg/ml trypsin solution, and oxidative degradation in 3% hydrogen peroxide ($H_2O_2$). The results of these evaluations are presented in Table 1, below.

TABLE 1

Characterization of Various Crosslinked Collagen Compositions

| Material | DSC (Tm ° C.) | Solubilization in Trypsin Solution | Oxidative Degradation in 3% $H_2O_2$ |
| --- | --- | --- | --- |
| DSS-ZI | 74.3 | 7 days | 14 days |
| DSS-MC | 57.7 | 2 days | N/A |
| $BS^3$-ZI | 67.6 | N/A | N/A |
| $BS^3$-MC | 58.6/64 | N/A | N/A |
| SEPEG-ZI | N/A | 3 days | 10 days |
| SEPEG-MC | N/A | 16 hours | N/A |
| SGPEG-ZI | 60.8 | 3 days | 7 days |
| SGPEG-MC | N/A | 16 hours | N/A |

ZI = Zyderm ® I Collagen (35 mg/ml collagen concentration)
MC = methylated collagen (21 mg/ml collagen concentration)
DSS = disuccinimidyl suberate
$BS^3$ = bis(sulfosuccinimidyl) suberate
SEPEG = difunctionally activated SE-PEG (n = 2, 3800 MW)
SGPEG = difunctionally activated SG-PEG (3800 MW)
N/A = Data not available.

Differential scanning calorimetry (DSC) is used to measure denaturational transitions in collagen, which can be used to assess the relative strength of crosslinking achieved. As indicated by the DSC results above, crosslinking of fibrillar collagen by the hydrophobic crosslinking agents DSS and $BS^3$ is at least as strong as that achieved using the hydrophilic crosslinking agent SG-PEG. Slightly lower numbers were obtained for the methylated (nonfibrillar) collagen formulations.

Solubilization in trypsin solution was determined by incubating a 5-mm thick disk of each crosslinked material at 37° C. in a solution comprising 1 mg trypsin in 1 ml water and measuring how much time was required to disperse the crosslinked collagen gel. As shown above, approximately twice as much time (7 days) was required to solubilize the DSS-ZI gel as was required to solubilize the SEPEG-ZI and SGPEG-ZI gels (3 days each), indicating that DSS achieves stronger crosslinking (i.e., increased crosslinking density) to fibrillar collagen than do either SE-PEG or SG-PEG. The methylated collagen formulations demonstrated less stability in trypsin solution in general, but the methylated collagen formulations crosslinked using DSS showed considerable improvement in stability over those crosslinked using either SE-PEG or SG-PEG.

Oxidative degradation was determined by incubating a 5-mm thick disk of each crosslinked material at 37° C. in a 3% solution of hydrogen peroxide in water and measuring how much time was required to disperse the crosslinked collagen gel. As with the results of the trypsin solubilization described above, nearly twice as much time (14 days) was required to solubilize the DSS-ZI gel as was required to solubilize the SEPEG-ZI (10 days) and SGPEG-ZI gels (7 days), indicating that DSS achieves stronger crosslinking to fibrillar collagen than do either SE-PEG or SG-PEG. Thus, with regard to trypsin sensitivity and susceptibility to oxidative degradation, the collagen materials crosslinked using hydrophobic crosslinking agents showed considerable and unexpected improvement over those crosslinked with the hydrophilic crosslinking agents previously described in the art.

Example 2

In vivo Persistence of Crosslinked Collagen Compositions

Crosslinked collagen formulations were prepared fresh by mixing the contents of a 1-cc syringe containing 1.0 gram of a mixture of Zyplast® (glutaraldehyde-crosslinked collagen having a collagen concentration of 35 mg/ml, available from Collagen Corporation, Palo Alto, Calif.) and Zyderm® Collagens (in a 70:30 weight/ weight ratio) with the contents of a 1-cc syringe containing either 3 mg of DSS, 3 mg of SE-PEG, or 3 mg of SG-PEG. A noncrosslinked mixture of Zyplast and Zyderm Collagens in a 70:30 weight ratio was used as the control. Two groups consisting of 24 male Sprague-Dawley rats each were injected with implants consisting of 0.5 milliliters each of two of the four formulations, according to the schedule below.

Animal Group A:

Site 1 Zyplast/Zyderm Collagen mixture (control)

Site 2 Zyplast/Zyderm Collagen mixture crosslinked using DSS

Animal Group B

Site 1 Zyplast/Zyderm Collagen mixture crosslinked using SG-PEG

Site 2 Zyplast/Zyderm Collagen mixture crosslinked using SE-PEG

The materials were injected subcutaneously through a 27-gauge needle within approximately 5 minutes of mixing the collagen and crosslinking agent.

Six animals from each of Groups A and B were sacrificed at each of the 7, 14, 28, and 90 day post-implantation time points. The implants with surrounding tissue were excised and examined histologically. The injected crosslinked materials had assumed a discrete, football-shaped, bolus-like configuration, whereas the noncrosslinked formulation was present as a more diffuse mass. The implants from four animals out of each group were used for histology studies and wet weight experiments. The implants from two animals out of each group were used to measure the mechanical force required to dislodge the implant from the host tissue. The results of the histology studies and wet weight experiments are discussed below.

The excised implants were examined histologically and scored on a scale of 0 through 4 on each of three parameters: inflammatory infiltrate, fibroblast ingrowth, and fibrosis. A score of 4 indicated the presence of a maximum amount of a parameter; a score of 0 indicated that the particular parameter was not observed in connection with the implant being examined (i.e., a score of 0 on inflammatory infiltrate indicates that no inflammatory infiltrate was observed in the implant site). Results of the histological examinations are presented in Tables 2, 3, and 4, and discussed below. Average scores are listed in parentheses.

TABLE 2

| Implant Material | Inflammatory Infiltrate | | | |
|---|---|---|---|---|
| | Day 7 | Day 14 | Day 28 | Day 90 |
| Z/Z | 0, 2, 2, 1 (1.25) | 2, 0, 0 (0.67) | 0, 0, 0, 1 (0.25) | 0, 0, 0, 0 (0) |
| Z/Z + DSS | 1, 2, 2, 3, 2 (2,0) | 3, 3, 1 (2.3) | 1, 1, 1, 1 (1.0) | 0, 0, 0, 0 (0) |
| Z/Z + SG-PEG | 1, 1, 1 (1.0) | 0, 1, 3, 1 (1.25) | 1, 0, 2, 1 (1.0) | 0, 0, 0, 0 (0) |
| Z/Z + SE-PEG | 1, 1, 1, 2 (1.25) | 0, 1, 1, 1 (0.75) | 1, 0, 2, 2 (1.25) | 0, 0, 0, 0 (0) |

Z/Z = mixture of Zyplast ® and Zyderm ® I Collagens in a 70:30 weight/weight ratio
DSS = disuccinimidyl suberate
BS$^3$ = bis(sulfosuccinimidyl) suberate
SEPEG = difunctionally activated SE-PEG (n = 2, 3800 MW)
SGPEG = difunctionally activated SG-PEG (3800 MW)

At days 7 and 14, the collagen implants crosslinked using DSS showed a moderate inflammatory response, slightly greater than the responses observed for the other (crosslinked and noncrosslinked) collagen compositions. By day 28, inflammatory infiltrate into the DSS-crosslinked implant was minimal, diminishing to nonexistent by day 90.

TABLE 3

| Implant Material | Fibroblast Ingrowth | | | |
|---|---|---|---|---|
| | Day 7 | Day 14 | Day 28 | Day 90 |
| Z/Z | 0, 0, 0, 0 (0) | 1, 1, 1 (1.0) | 1, 0, 0, 1 (0.5) | 0, 0, 1, 1 (0,5) |
| Z/Z + DSS | 0, 0, 0, 0, 0 (0) | 0, 0, 0 (0) | 0, 0, 0, 0 (0) | 0, 0, 0, 0 (0) |
| Z/Z + SG-PEG | 0, 0, 0 (0) | 1, 1, 1, 1 (1.0) | 1, 0, 2, 1 (1.0) | 0, 1, 1, 1 (0.75) |
| Z/Z + SE-PEG | 0, 0, 0, 0 (0) | 1, 1, 1, 0 (0.75) | 1, 0, 2, 2 (1.25) | 0, 0, 0, 1 (0.25) |

Unlike the other crosslinked and noncrosslinked collagen formulations, the DSS-crosslinked implants showed no evidence of fibroblast ingrowth throughout the entire duration of the study. This is most likely due to the very tight crosslinked collagen network achieved using DSS as a crosslinking agent.

TABLE 4

| Implant Material | Fibrosis | | | |
|---|---|---|---|---|
| | Day 7 | Day 14 | Day 28 | Day 90 |
| Z/Z | 0, 1, 1, 2 (1.0) | 1, 0, 0 (0.33) | 0, 0, 1, 0 (0.25) | 0, 0, 0, 0 (0) |
| Z/Z + DSS | 1, 0, 2, 1, 2 (1.2) | 1, 0, 1 (0.67) | 0, 0, 1, 1 (0.5) | 0, 0, 0, 0 (0) |
| Z/Z + SG-PEG | 0, 1, 1 (0.67) | 1, 1, 1, 1 (1.0) | 1, 1, 1, 1 (1.0) | 0, 0, 0, 0 (0) |
| Z/Z + SE-PEG | 1, 0, 2, 1 (1.25) | 0, 1, 1, 1 (0.75) | 0, 1, 1, 1 (0.75) | 0, 0, 0, 0 (0) |

Fibrosis was observed to be similar in all three of the crosslinked collagen compositions examined.

Figure 8:
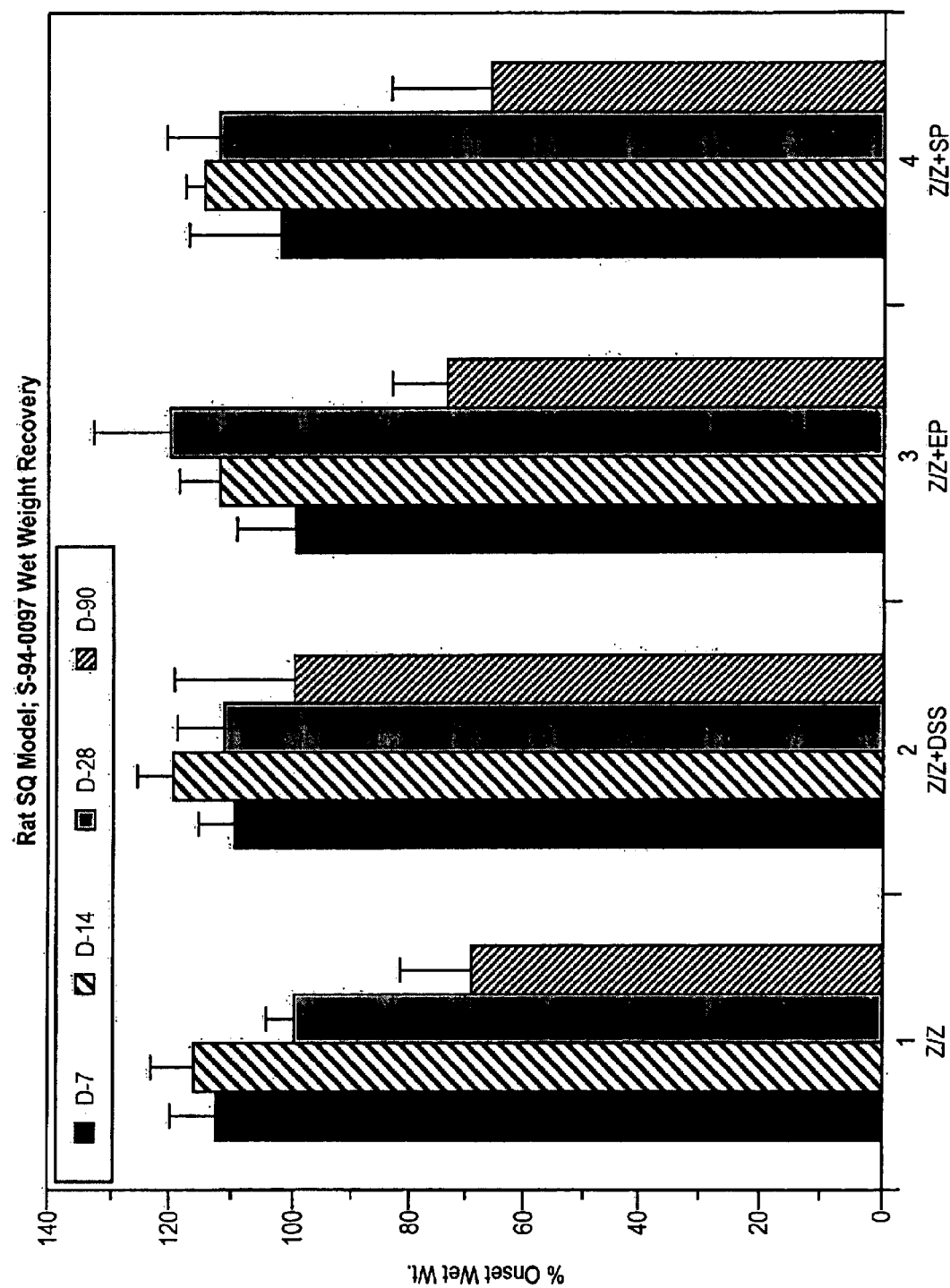
FIG. 8 is a bar graph illustrating the wet weight recovery of implants of various compositions at day 7 (solid-bars), day 14 (hatched bars, heavy lines), day 28 (stippled bars) and day 90 (hatched bars, light lines).

Each of the implants was weighed following explantation. Wet weight of the implant as a percentage of the original weight of the implant is shown in FIG. 8 for each of the four formulations at each time point. There were no significant differences between any of the formulations at the 7, 14, and 28 day time points. However, at the 90-day time point, the collagen formulation crosslinked using DSS showed significantly better retention of wet weight (close to 100 percent) than the other formulations. Due to the lack of fibroblast ingrowth seen during histological examination, the wet weight of the DSS-crosslinked implant is believed to consist substantially of the implant material itself rather than invading cells. This observation indicates that the DSS-crosslinked collagen implants were not resorbed into the host tissue as quickly as the other collagen implant materials, possibly due to the tightly crosslinked network achieved using DSS as a crosslinking agent.

At each of the 7, 28, and 90-day time points of the study, the portion of the skin containing the implant was excised from two animals from each of Groups A and B. The skin surrounding the implant was trimmed into a uniform rectangular shape having dimensions of 2 cm×4 cm. The encapsulated tissue that had grown over the surface of the implant was removed so that the implant now appeared to be merely resting on the surface of the dermis.

Figure 9:
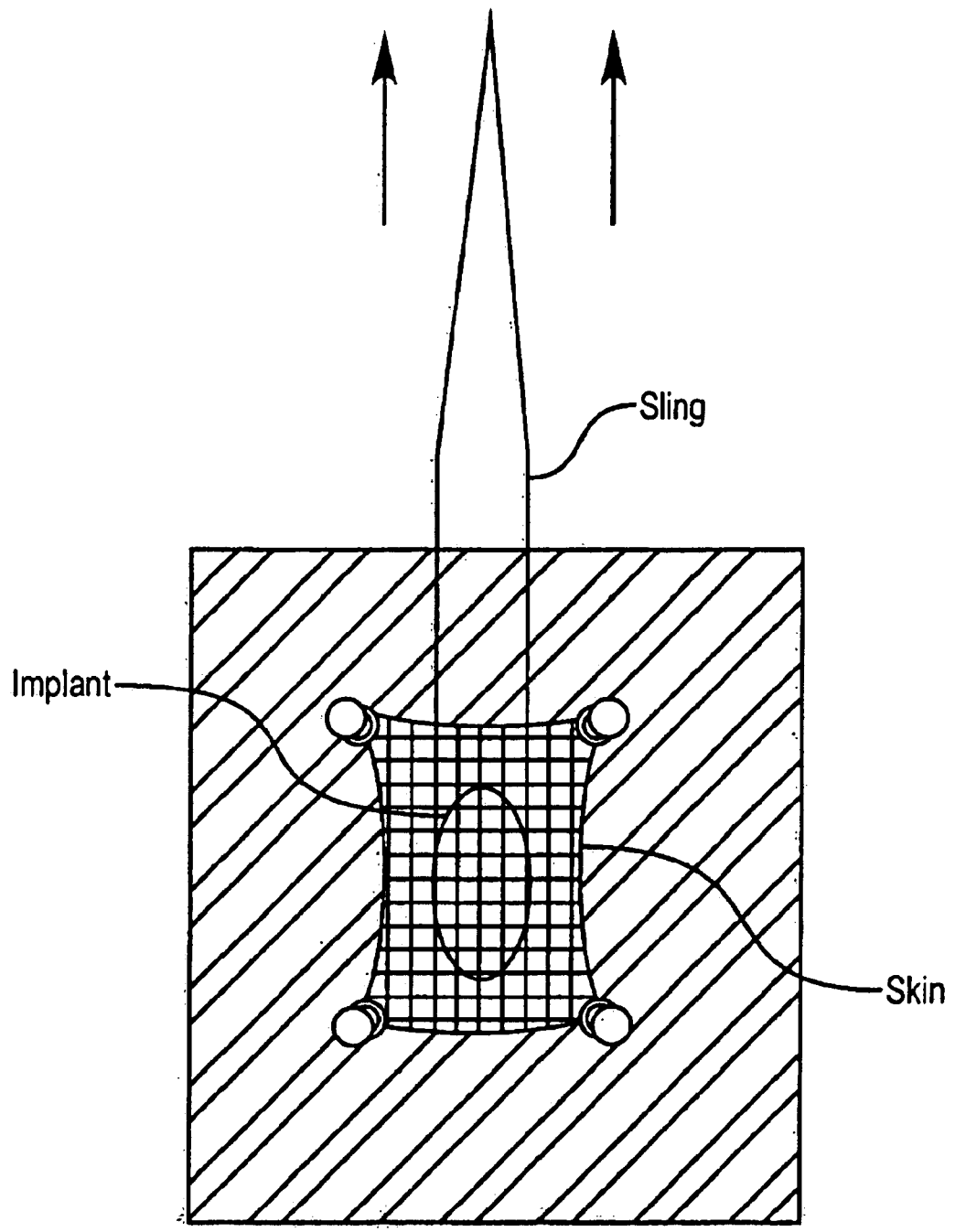
FIG. 9 depicts the method used to measure the mechanical force required to dislodge implants of various compositions from the surrounding tissues. The arrows indicate the direction of the applied force.
Figure 10:
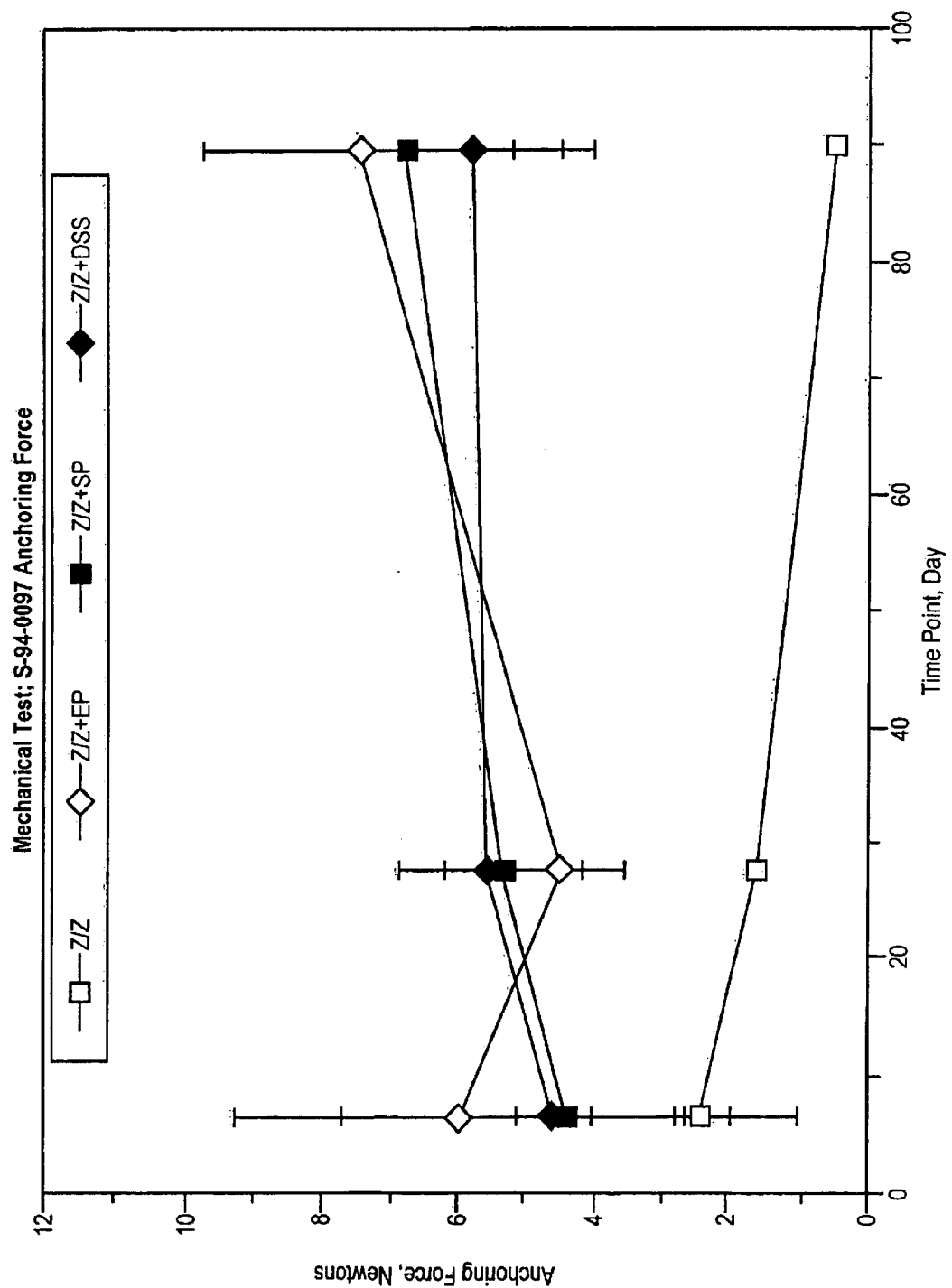
FIG. 10 is a graph showing the anchoring force, in newtons, of implants of various compositions removed at days 7, 14, 28 and 90.

The piece of skin containing the implant was pinned to a 3 cm×5 cm wooden board using one thumbtack at each of the four corners of the skin. As illustrated in FIG. 9, a sling was placed externally around the perimeter of the implant. The mechanical force required to dislodge the implant from the tissue was measured using the Instron Universal Tester, Model 4202, by holding the wooden board (to which the piece of skin was attached) in one of the Instron's clamps and holding the end of the sling in the other clamp. The Instron pulled on the clamp holding the sling until the implant broke free from the tissue. Force anchoring to tissue is depicted graphically in FIG. 10 for each of the four formulations at the 7, 28, and 90-day time points. There were no significant differences between the formulations crosslinked using the hydrophobic crosslinking agent (DSS) and the formulations crosslinking using either of the hydrophilic crosslinking agents (SE-PEG; SG-PEG).

Example 3

Preparation and Characterization of Crosslinked Biomaterial Compositions Containing Mixtures of Hydrophobic and Hydrophilic Crosslinking Agents Fibrillar collagen (Zyderm® I Collagen, 35 mg/ml collagen concentration, available from Collagen Corporation, Palo Alto, Calif.) was crosslinked using disuccinimidyl suberate (DSS), difunctionally activated SE-PEG (n=2, 3800 MW), and a 50:50 (weight/weight) mixture of DSS and difunctionally activated SE-PEG. The crosslinked collagen formulations were prepared by mixing the contents of a 5-cc syringe containing 5.0 grams of Zyderm Collagen with the contents of a 5-cc syringe containing either 15 mg of DSS, 15 mg of SE-PEG, or 15 mg of the DSS/SE-PEG mixture.

All of the crosslinking agents were used in dry form. The DSS/SE-PEG mixture was prepared immediately prior to crosslinking by placing 7.5 mg each of DSS and SE-PEG into a 5-cc syringe, then shaking the syringe by hand to mix the two crosslinking agents.

The collagen and crosslinking agent were mixed by passing the material between the two syringes using a 3-way stopcock, employing about 40 to 50 passes of material between the syringes. Once adequate mixing of the collagen and crosslinking agent had been achieved, the material was transferred into one syringe and incubated at 37° C. for approximately 16 hours.

Each of the three crosslinked collagen materials prepared as described above was extruded out of the plunger end of its syringe. The resulting crosslinked cylindrical gels were then sectioned into 5-mm thick disks. The three formulations were evaluated using differential scanning calorimetry (DSC). The gel strength of each formulation was measured using the Instron Universal Tester, Model 4202. DSC and gel strength results for each of the three crosslinked collagen formulations are presented in Table 5, below.

TABLE 5

DSC and Gel Strength Results for Various Crosslinked Collagen Compositions

| Crosslinking Agent | DSC (° C.) | Gel Strength (Newtons) | Average Gel Strength (Newtons) | S.D. |
|---|---|---|---|---|
| DSS | 74.3 | 54.1 | 46.5 | 6.0 |
|  |  | 40.5 |  |  |
|  |  | 45.0 |  |  |
|  |  | 41.5 |  |  |
|  |  | 51.1 |  |  |
| SE-PEG | 59.5 | 59.4 | 58.6 | 2.5 |
|  |  | 56.4 |  |  |
|  |  | 56.2 |  |  |
|  |  | 58.7 |  |  |
|  |  | 62.4 |  |  |
| DSS/SE-PEG | 53–65* | 28.1 | 41.7 | 8.2 |
|  | 65–80** | 43.9 |  |  |
|  |  | 44.2 |  |  |
|  |  | 50.3 |  |  |
|  |  | 42.3 |  |  |

*Broad main peak.
**Broad shoulder peak.

The inconsistency in the DSC and gel strength results for the collagen composition prepared using a mixture of hydrophobic and hydrophilic crosslinking agents may be due to several factors, among them: insufficient mixing of the two crosslinking agents prior to mixing with collagen, the heterogeneous nature of the composition itself, and, possibly, a ratio of crosslinking agents that had not been optimized. Another factor may be that the SE-PEG is able to crosslink collagen more quickly-than DSS due to the lower solubility of the DSS in the aqueous solution in which the collagen fibers are suspended.

Collagen compositions prepared using mixtures of hydrophobic and hydrophilic crosslinking agents may be useful in certain therapeutic applications due to the relative contributions of the two different types of crosslinking agent to the properties of the final composition: the hydrophobic crosslinking agent, increased stability; the hydrophilic crosslinking agent, increased elasticity and better overall handling properties.

It is not intended that the invention be limited by the preferred embodiments described above, which are used for purposes of illustration. The invention is intended to have the scope defined by the attached claims.

What is claimed is:

1. An injectable, crosslinkable composition that crosslinks in situ following administration to a patient to form a heterogeneous, crosslinked biomaterial composition, comprising:
   a biomaterial comprised of a biocompatible polymer containing nucleophilic groups;
   a hydrophobic crosslinking agent containing up to about 14 carbon atoms and comprised of a polyacid esterified with a reactive moiety selected from the group consisting of succinimidyl and sulfosuccinimidyl groups; and
   a hydrophilic crosslinking agent, wherein both the hydrophobic crosslinking agent and the hydrophilic crosslinking agent crosslink the biomaterial in situ following administration of the composition to a patient, but are not reactive with respect to each other.

2. The composition of claim 1, further including water, such that the composition is comprised of an aqueous suspension.

3. The composition of claim 1, wherein the nucleophilic groups are primary amino groups.

4. The composition of claim 1, wherein the biomaterial is selected from the group consisting of collagen, glycosaminoglycans, and mixtures thereof.

5. The composition of claim 4, wherein the biomaterial is comprised of collagen.

6. The composition of claim 5, wherein the collagen is fibrillar collagen.

7. The composition of claim 5, wherein the collagen is nonfibrillar collagen.

8. The composition of claim 7, wherein the non-fibrillar collagen is comprised of chemically derivatized collagen selected from the group consisting of succinylated collagen and methylated collagen.

9. The composition of claim 8, wherein the collagen is succinylated collagen.

10. The composition of claim 8, wherein the collagen is methylated collagen.

11. The composition of claim 5, wherein the collagen is selected from the group consisting of Type I collagen, Type II collagen, Type III collagen, Type IV collagen, and mixtures thereof.

12. The composition of claim 11, wherein the collagen is Type I collagen.

13. The composition of claim 5, wherein the collagen is telopeptide collagen.

14. The composition of claim 5, wherein the collagen is atelopeptide collagen.

15. The composition of claim 5, wherein the collagen is denatured collagen.

16. The composition of claim 4, wherein the biomaterial is a glycosaminoglycan.

17. The composition of claim 16, wherein the glycosaminoglycan is selected from the group consisting of hyaluronic acid, chondroitin sulfate A, chondroitin sulfate C, dermatan sulfate, keratan sulfate, keratosulfate, chitin, chitosan, heparin, and derivatives thereof.

18. The composition of claim 1, wherein the hydrophobic crosslinking agent is disuccinimidyl suberate.

19. The composition of claim 1, wherein the hydrophobic crosslinking agent is comprised of a polyacid containing two, three or four carboxylic acid groups each esterified with a succinimidyl group.

20. The composition of claim 19, wherein the polyacid is selected from the group consisting of trimethylolpropane tricarboxylic acid, di(trimethylol propane) tetracarboxylic acid, heptanedioic acid, suberic acid and hexadecanedioic acid.

21. The composition of claim 1, wherein the hydrophobic crosslinking agent is comprised of a polyacid containing two, three or four carboxylic acid groups each esterified with a sulfosuccinimidyl group.

22. The composition of claim 21, wherein the polyacid is selected from the group consisting of trimethylolpropane tricarboxylic acid, di(trimethylol propane) tetracarboxylic acid, heptanedioic acid, suberic acid and hexadecanedioic acid.

23. The composition of claim 1, wherein the hydrophobic crosslinking agent is selected from the group consisting of disuccinimidyl suberate, dithiobis(succinimidyl-propionate, bis(sulfosuccinimidyl) suberate, bis(2-succinimidooxycarbonyloxy)ethyl sulfone, and 3,3'-dithiobis(sulfosuccinimidylpropionate).

24. The composition of claim 1, wherein the hydrophilic crosslinking agent is comprised of an activated hydrophilic polymer.

25. The composition of claim 24, wherein the activated hydrophilic polymer is selected from the group consisting of polyethylene glycol succinimidyl glutarate, polyethylene glycol succinimidyl, polyethylene glycol succinimidyl succinamide, and polyethylene glycol succinimidyl carbonate.

26. The composition of claim 24, wherein the activated hydrophilic polymer is polyethylene glycol succinimidyl glutarate.

27. The composition of claim 24, wherein the activated hydrophilic polymer is polyethylene glycol succinimidyl.

28. A kit for administering an in situ crosslinkable composition to a patient via injection, comprising:
 a first syringe containing a biomaterial comprised of a biocompatible polymer containing nucleophilic groups;
 a second syringe containing a mixture of a hydrophilic crosslinking agent and a hydrophobic crosslinking agent containing up to about 14 carbon atoms and comprised of a polyacid esterified with reactive moieties selected from the group consisting of succinimidyl groups and sulfosuccinimidyl groups, wherein both the hydrophobic crosslinking agent and the hydrophilic crosslinking agent crosslink the biomaterial in situ following administration of a combination of the biomaterial and the crosslinking agents to a patient, but are not reactive with respect to each other.

29. The kit of claim 28, wherein the first syringe further contains water, such that the biomaterial is in an aqueous suspension.

30. The kit of claim 28, wherein the nucleophilic groups are primary amino groups.

31. The kit of claim 28, wherein the biomaterial is selected from the group consisting of collagen, glycosaminoglycans, and mixtures thereof.

32. The kit of claim 31, wherein the biomaterial is comprised of collagen.

33. The kit of claim 32, wherein the collagen is fibrillar collagen.

34. The kit of claim 32, wherein the collagen is nonfibrillar collagen.

35. The kit of claim 34, wherein the nonfibrillar collagen is comprised of chemically derivatized collagen selected from the group consisting of succinylated collagen and methylated collagen.

36. The kit of claim 35, wherein the collagen is succinylated collagen.

37. The kit of claim 35, wherein the collagen is methylated collagen.

38. The kit of claim 32, wherein the collagen is selected from the group consisting of Type I collagen, Type II collagen, Type III collagen, Type IV collagen, and mixtures thereof.

39. The kit of claim 38, wherein the collagen is Type I collagen.

40. The kit of claim 32, wherein the collagen is telopeptide collagen.

41. The kit of claim 32, wherein the collagen is atelopeptide collagen.

42. The kit of claim 32, wherein the collagen is denatured collagen.

43. The kit of claim 31, wherein the biomaterial is a glycosaminoglycan.

44. The kit of claim 43, wherein the glycosaminoglycan is selected from the group consisting of hyaluronic acid, chondroitin sulfate A, chondroitin sulfate C, dermatan sulfate, keratan sulfate, keratosulfate, chitin, chitosan, heparin, and derivatives thereof.

45. The kit of claim 28, wherein the hydrophobic crosslinking agent is comprised of a polyacid containing two, three or four carboxylic acid groups each esterified with a succinimidyl group.

46. The kit of claim 28, wherein the hydrophobic crosslinking agent is comprised of a polyacid containing two, three or four carboxylic acid groups each esterified with a sulfosuccinimidyl group.

47. The kit of claim 45, wherein the polyacid is selected from the group consisting of trimethylolpropane tricarboxylic acid, di(trimethylol propane) tetracarboxylic acid, heptanedioic acid, suberic acid and hexadecanedioic acid.

48. The kit of claim 46, wherein the polyacid is selected from the group consisting of trimethylolpropane tricarboxylic acid, di(trimethylolpropane) tetracarboxylic acid, heptanedioic acid, suberic acid and hexadecanedioic acid.

49. The kit of claim 28, wherein the hydrophobic crosslinking agent is selected from the group consisting of disuccinimidyl suberate, dithiobis(succinimidylpropionate, bis(sulfosuccinimidyl) suberate, bis(2-succinimidooxycarbonyloxy)ethyl sulfone, and 3,3-dithiobis(sulfosuccinimidylpropionate).

50. The kit of claim 49, wherein the hydrophobic crosslinking agent is disuccinimidyl suberate.

51. The kit of claim 28, wherein the hydrophilic crosslinking agent is comprised of an activated hydrophilic polymer.

52. The kit of claim 51, wherein the activated hydrophilic polymer is selected from the group consisting of polyethylene glycol succinimidyl glutarate, polyethylene glycol succinimidyl, polyethylene glycol succinimidyl succinamide, and polyethylene glycol succinimidyl carbonate.

53. The kit of claim 52, wherein the activated hydrophilic polymer is polyethylene glycol succinimidyl glutarate.

54. The kit of claim 52, wherein the activated hydrophilic polymer is polyethylene glycol succinimidyl.

* * * * *